(12) United States Patent
Moskal

(10) Patent No.: US 10,366,210 B2
(45) Date of Patent: Jul. 30, 2019

(54) MEDICAL DEVICE CONNECTION STATUS MONITORING

(71) Applicant: Fenwal, Inc., Lake Zurich, IL (US)

(72) Inventor: Witold Moskal, Park Ridge, IL (US)

(73) Assignee: Fenwal, Inc., Lake Zurich, IL (US)

( * ) Notice: Subject to any disclaimer, the term of this patent is extended or adjusted under 35 U.S.C. 154(b) by 142 days.

(21) Appl. No.: 15/601,279

(22) Filed: May 22, 2017

(65) Prior Publication Data

US 2017/0351841 A1    Dec. 7, 2017

Related U.S. Application Data

(60) Provisional application No. 62/345,099, filed on Jun. 3, 2016.

(51) Int. Cl.

| | |
|---|---|
| *G06F 15/173* | (2006.01) |
| *G06F 19/00* | (2018.01) |
| *G16H 10/60* | (2018.01) |
| *G16H 50/80* | (2018.01) |
| *G16H 40/40* | (2018.01) |

(Continued)

(52) U.S. Cl.

CPC ........ *G06F 19/3468* (2013.01); *A61B 5/0031* (2013.01); *A61M 5/142* (2013.01); *G16H 10/60* (2018.01); *G16H 20/17* (2018.01); *G16H 40/40* (2018.01); *G16H 40/63* (2018.01); *G16H 40/67* (2018.01); *G16H 50/80* (2018.01); *A61B 5/742* (2013.01); *A61M 5/172* (2013.01); *A61M 2205/18* (2013.01); *A61M 2205/3576* (2013.01); *A61M 2205/3584* (2013.01);

(Continued)

(58) Field of Classification Search

USPC .......................................................... 709/224

See application file for complete search history.

(56) References Cited

U.S. PATENT DOCUMENTS

| | | |
|---|---|---|
| 2004/0138835 A1 | 7/2004 | Ransom |
| 2009/0177769 A1* | 7/2009 | Roberts ................... G06F 19/00 709/224 |

(Continued)

OTHER PUBLICATIONS

Extended European Search Report for application No. 17171535.2, dated Nov. 6, 2017, 12 pages.

(Continued)

*Primary Examiner* — Hee Soo Kim

(74) *Attorney, Agent, or Firm* — Cook Alex Ltd.

(57) ABSTRACT

A computer configured to monitor medical device data for presentation on a user interface. The computer comprises a processing circuit and a network interface circuit configured to provide communications over a network. The processing circuit is configured to receive at configurable time intervals a medical device status message from a medical device over the network; set a device last connection time, comprising a date and time that a most recent status message was received over the network by the computer from the medical device; receive input from a user interface in communication with the computer to retrieve pump information; calculate a delta between the device last connection time and a date and time the processing circuit received the input from the user interface; compare the delta with a device connection threshold value; and display a warning on the user interface if the delta is greater than the threshold value.

18 Claims, 7 Drawing Sheets

(51) Int. Cl.
    *A61B 5/00*     (2006.01)
    *A61M 5/142*     (2006.01)
    *G16H 40/63*     (2018.01)
    *G16H 40/67*     (2018.01)
    *G16H 20/17*     (2018.01)
    *A61M 5/172*     (2006.01)
    *G16H 50/30*     (2018.01)

(52) U.S. Cl.
    CPC ... *A61M 2205/50* (2013.01); *A61M 2205/502* (2013.01); *G16H 50/30* (2018.01)

(56) References Cited

U.S. PATENT DOCUMENTS

| | | |
|---|---|---|
| 2010/0174229 A1 | 7/2010 | Hsu et al. |
| 2013/0031201 A1 | 1/2013 | Kagan |
| 2015/0371198 A1 | 12/2015 | Jensen et al. |

OTHER PUBLICATIONS

Communication pursuant to Article 94(3) EPC for application No. 17171535.2, dated Jun. 26, 2018, 7 pages.

\* cited by examiner

| DEVICES ☐ PUMPS | | | NOT FOR HUMAN USE | | | EXPORT PUMPS |
|---|---|---|---|---|---|---|
| PUMPS | | | | | | |
| LOCATIONS: ALL ⌄ | DEVICE TYPE: ALL ⌄ | FILTER BY SERIAL OR INVENTORY NUMBER | | | | |
| HOSPITAL | SERIAL NUMBER ⌄ | DEVICE TYPE | TARGET DATA SET | ACTIVE DATA SET | LAST CONNECTION | MAC ADDRESS |
| GERI_HOSPITAL A1 | Z019735 /10150403 | AGILIA VP MC | DOUG 2015-11-11v2-000 | DOUG 2015-11-11v2-000 | 11/17/2015 9:56 | 00:23:a7:0c:11:c5 |
| GERI_HOSPITAL B1 | Z019735 /01010101 | AGILIA VP MC | DOUG 2015-11-11v2-000 | DOUG 2015-11-11v2-000 | 11/17/2015 9:56 | 00:23:a7:0c:11:85 |
| GERI_HOSPITAL C1 | Z018735 /10150429 —10a | AGILIA SP MC | ⊙DOUG 2015-11-11v2-000 | DOUG 2015-11-05v2-000 | 11/10/2015 11:18 —42 | 00:23:a7:0c:11:67 |
| 50 | | | | 47 | | |

FIG. 3

MEDICAL DEVICE CONNECTION STATUS MONITORING

CROSS-REFERENCE TO RELATED APPLICATIONS

This application claims the benefit of U.S. Provisional Patent App. No. 62/345,099 filed Jun. 3, 2016, which is expressly incorporated herein by reference in its entirety.

FIELD OF THE DISCLOSURE

The present disclosure is directed to monitoring network connection status. More specifically, the present disclosure relates to methods, systems, and apparatus to facilitate monitoring of connection status between medical devices and their data management system.

BACKGROUND

Infusion pumps are used in the field of medicine to administer drugs to patients often over an extended time period. The time period of infusion may be longer than can be managed easily by direct injection. Sophistication in drug delivery has increased as availability of drugs, therapeutic techniques, and technological capabilities have improved. Achieving this sophistication in drug delivery capability and maintaining ease of use have become more important for infusion pump manufacturers.

Infusion pumps are used to administer drugs and other medicaments often in a clinical setting. An infusion pump may provide a controlled amount of the medicament over time to the patient. The amount may be administered pursuant to parameters entered, for example, by a clinician into the pump using a pump user interface.

To avoid errors in drug administration, some infusion pumps may hold a library of drug names and associated parameters, e.g., rate of infusion, frequency of infusion, etc. The drug library may be created and/or updated by a health care professional and/or health center employee and be accessed and be made accessible to a health care professional by a data management server. In some cases, overriding or reprogramming of parameters programmed into the drug library may be desired. Given the interactive and interrelated nature of infusion pumps, data management systems, drug libraries, and health care professionals, greater reliability and availability of information among different components may be desired.

SUMMARY

According to an exemplary embodiment, the present disclosure is directed to a server computer configured to monitor and process medical device data for presentation on a user interface. The server computer comprises a network interface circuit configured to provide communications over a network and also comprises a processing circuit. The processing circuit is configured to receive at configurable time intervals a medical device status message from a medical device over the network; set a device last connection time, comprising a date and time that a most recent status message was received over the network by the server computer from the medical device; receive input from a user interface in communication with the server computer to retrieve pump information; calculate a delta between the device last connection time and a date and time the processing circuit received the input from the user interface; compare the delta with a device connection threshold value; and display a warning indicator on the user interface if the delta is greater than the device connection threshold value.

According to an exemplary embodiment, the present disclosure is directed to computer-implemented medical device management method for monitoring connection status between medical devices and their data management server computer over a network. The method comprises receiving at configurable time intervals via a processing circuit a medical device status message from a medical device over the network; setting a device last connection time, comprising a date and time that a most recent status message was received over the network by the server computer from the medical device; receiving input from a user interface in communication with the server computer to retrieve pump information; calculating a delta between the device last connection time and a date and time the server computer received the input from the user interface; comparing the delta with a device connection threshold value; and displaying a warning indicator on the user interface if the delta is greater than the device connection threshold value.

According to an exemplary embodiment, the present disclosure is directed to a computer-implemented medical device management system comprising a data management system comprising analog and/or digital circuit components comprising discrete circuit elements and/or programmed integrated circuits. The medical device management system also comprises a medical device comprising a network interface circuit configured to provide communications over a network with another medical device and/or with the data management system. The data management system is configured to receive at configurable time intervals a medical device status message from the medical device over the network; set a device last connection time, comprising a date and time that a most recent status message was received over the network by the data management system from the medical device; calculate a delta between the device last connection time and a date and time the data management system accesses information from the medical device; compare the delta with a device connection threshold value; and display a warning indicator on a user interface if the delta is greater than the device connection threshold value.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 3 is an illustration of content on a user interface displaying information for a medical device, according to an exemplary embodiment;

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The following discloses example methods, apparatus, systems, and articles of manufacture including, among other components, firmware and/or software executed on hardware. It should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only ways) to implement such methods, apparatus, systems, and/or articles of manufacture.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

One or more embodiments described herein may facilitate monitoring of connection status between medical devices and a data management system.

One or more embodiments described herein may enable a data management system to provide information to authorized users via a user interface regarding connection status between a medical device and the data management system.

Figure 1:
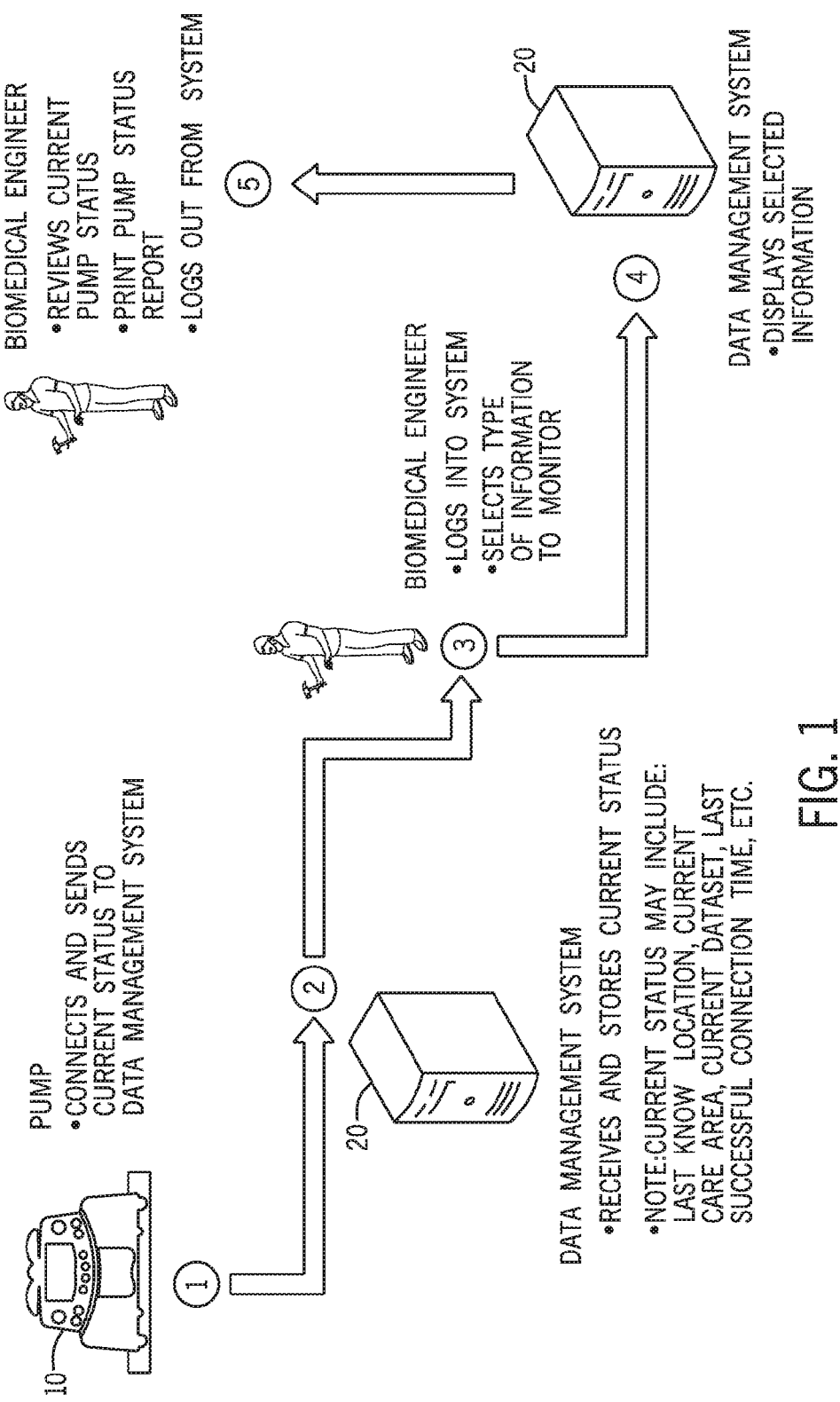
FIG. 1 is a flow diagram of a system for collecting data from a plurality of medical devices at a server computer, according to an exemplary embodiment.

Referring to FIG. 1, a flow diagram of a system for collecting data from a plurality of medical devices at a server computer is shown, according to an exemplary embodiment. The medical devices may comprise blood collection or apheresis devices, blood and/or biological fluid processing devices, therapeutic devices, infusion pumps, medical laboratory devices, drug delivery pumps, and/or other medical devices. In an embodiment in which the medical device is an infusion pump, the infusion pump 10 may be any of a variety of infusion pumps, such as a large volume infusion pump, a patient-controlled analgesia (PCA) pump, elastomeric pump, syringe pump, enteral or parenteral feeding pump, insulin pump, etc. At Step 1 in FIG. 1, infusion pump 10 may be configured to connect to and send current status to a data management system 20. Current status (e.g., connection status) may include, for example, the last known location of the infusion pump 10, the current care area of the pump 10, the current data set governing activity of the pump 10, the last successful connection time between the pump 10 and the data management system 20, and/or the status of any other parameter of the infusion pump 10.

At Step 2 in FIG. 1, infusion pump 10 may be configured for wired and/or wireless communication with a data management server computer 20. Each of pump 10 and server computer 20 may comprise a network interface circuit configured for network communications, such as a Wi-Fi circuit, Bluetooth circuit, Ethernet card, or other network interface circuit. Pump 10 may be configured to receive/transmit infusion pump data to and/or from server 20 over the respective network interface circuits. Server 20 may be configured to store the infusion data from a plurality of infusion pumps, which may be in different care areas, for analysis, whether automated or by a clinician. Infusion data transmissions may be initiated by infusion pump 10 and may occur periodically, intermittently, occasionally, every few minutes, several times per day, or at other regular or irregular frequencies. Infusion data stored at server 20 may be a complete set, or a subset of connection status data, that server 20 receives from pump 10.

At Step 3 in FIG. 1, an authorized user, such as a nurse, pharmacist, biomedical engineering staff, or other user may log into server 20 using a terminal (not shown), which may be a user interface for server 20 or may alternatively be a separate computing device or PC. The user opens an application configured to review infusion pump connection status data. Server 20 may be configured to generate one or more reports based on analysis of the infusion pump connection status data. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, loss of connection, etc.). The user may select one or more infusion data filters, such as hospital, data set, profile, drug, device type, infusion mode, time and/or date range, etc.

At Step 4 in FIG. 1, the server computer 20 may be configured to generate the selected infusion data report or reports. For example, the server computer 20 may generate the selected infusion data report or reports in response to input from the authorized user, automatically per a predetermined schedule, and/or a combination of both scenarios. At Step 5 in FIG. 1, the generated report is provided and/or made available to an authorized user to be analyzed.

Figure 2:
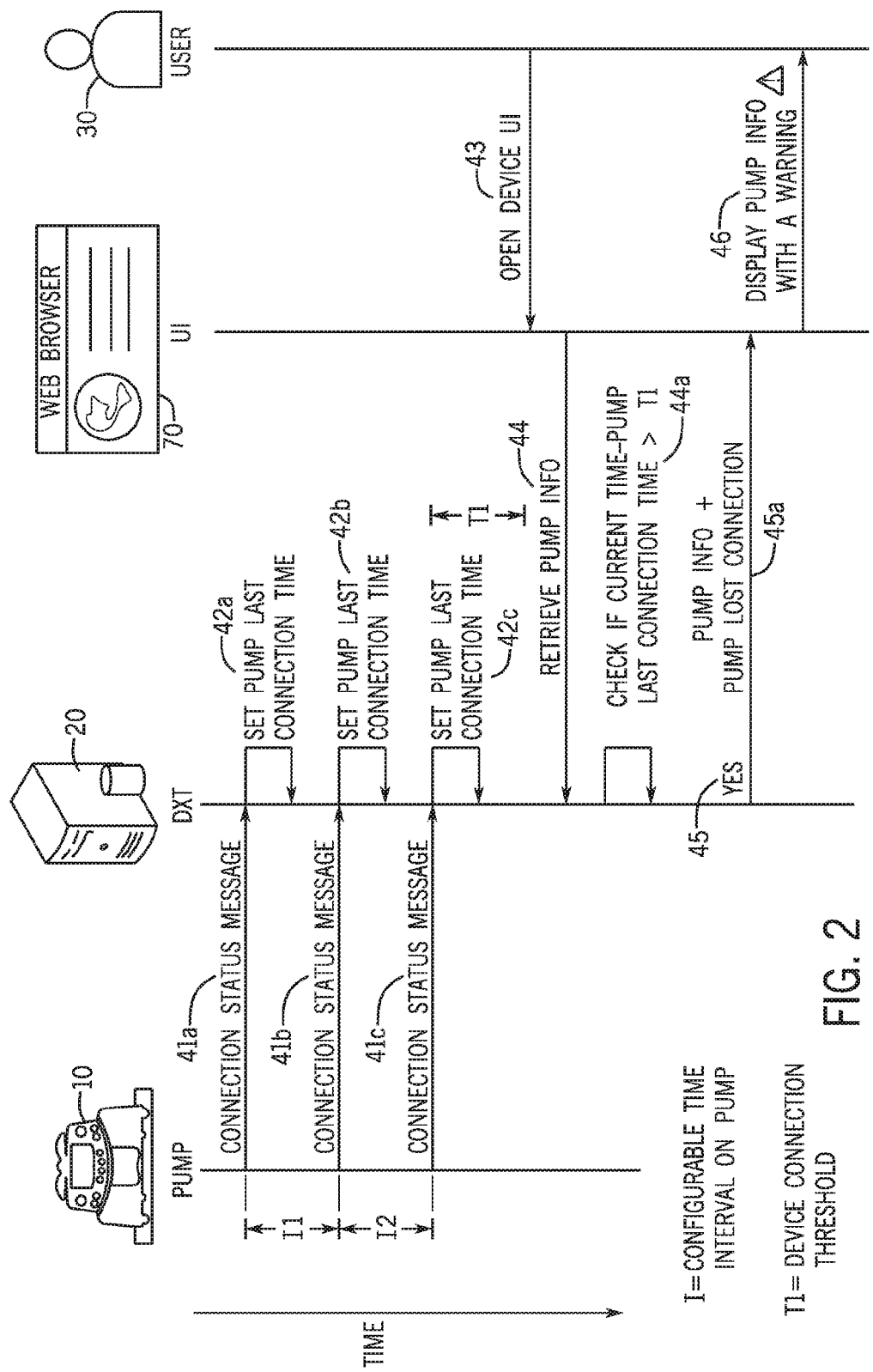
FIG. 2 is a schematic diagram of a UML sequence illustrating a method for monitoring connection status between a data management server computer and deployed pump(s) and displaying current status via a user interface to an authorized user, according to an exemplary embodiment.

FIG. 2 is a schematic diagram of a UML sequence illustrating a method for monitoring connection status between a data management server computer and deployed pump(s) and displaying current status via a user interface to an authorized user, according to an exemplary embodiment. In the embodiment shown in FIG. 2, a pump 10 is configured to connect to a data management system 20, which in turn is configured to connect to a user interface 70. An authorized user 30 may access the user interface 70 to check the status of the pump 10. The pump 10 may be configured to send a connection status message to the data management system 20 at configurable time intervals I1, I2. The connection status message may relay to the data management system 20 the current network connection status of the pump 10. The time intervals I1, I2 may be configured by an authorized user 30 and/or be pre-configured at default intervals at the manufacturing stage. The time intervals I1, I2 may be any suitable time interval (e.g. 500 milliseconds, 20 seconds, 1 minute, 10 minutes, etc.). Time interval I1 and time interval I2 may have same value or different values. For example, time interval I1, I2 may vary over a period of time or stay constant over a period of time. The time interval I1, I2 may vary, e.g., based on location, care area, ward, hospital, organization, geographic location, etc. The time interval I1, I2 may automatically change with different pump modes (e.g., in current active use mode, awake but inactive mode, sleep mode, standby mode, etc.). The time interval I1, I2 may vary depending on type of pump, e.g, volumetric pump, large volume pump, elastomeric pump, syringe pump, etc. The value of time interval I1, I2 may alternate or change over a period of time. For example, pump 10 may be configured to send a connection status message to the data management system 20 at alternating intervals of, e.g., 5 second and 10 seconds. In other embodiments, after at least a certain number of on-time connection status messages have been received successfully by the data management system 20 at shorter intervals, e.g, 5 seconds, pump 10 may be configured to send a connection status message to the data management system 20 at longer intervals, e.g., 10 seconds.

At step 41a in FIG. 2, the pump 10 may send a first connection status message to the data management system 20. At step 42a, the data management system 20 may set a pump last connection time, defined as the date and time that the most recent connection status message was successfully received over the network by the data management system 20 from the pump 10. The pump last connection time may be set in UTC (Coordinated UniversalTime) or any other suitable time standard. At time interval I1, I2 following the sending of the first connection status message of step 41a, the pump 10 may be configured to send a second connection status message to the data management system 20 at step 41b. At step 42b, the data management system 20 may again set a pump last connection time, this time designating the date and time that the second connection status message was received by the data management system 20. At time interval I1, I2 following the sending of the second connection status message of step 41b, the pump 10 may be configured to send a third connection status message to the data management system 20 at step 41c. At step 42c, the data management system 20 may again set a pump last connection time, this time designating the date and time that the third connection status message was received by the data management system 20. The pump 10 and the data management system 20 may be configured to continue this cycle of interaction for any suitable period of time, including for example, indefinitely and/or as specified by their programming.

A user 30 may access the user interface 70 at any time to view, retrieve, and/or modify pump information. Upon the user 30 accessing the user interface 70 connected to the data management system 20, the data management system 20 may be configured to calculate the delta between the current time and the pump last connection time. The data management system 20 may alternatively or also be configured to calculate the delta without user input. For example, the data management system 20 may automatically calculate the delta periodically and/or when the system 20 itself accesses the pump information.

Referring to FIG. 2, in one embodiment, a user 30 may open the user interface 70 at step 43, subsequent to the time point when the data management system 20 set the pump last connection time at step 42c to the time that the third connection status message was received by the data management system 20. Upon the user connecting to the user interface 70, the data management system 20 may be configured to retrieve at step 44 the pump last connection time. Retrieval of the pump last connection time may be followed by step 44a at which the system 20 is configured to compare the current time at the time of pump last connection time retrieval to the pump last connection time set in step 42c. The difference delta between the time of pump last connection time retrieval and the pump last connection time may then be compared to a device connection threshold value T1. The device connection threshold value T1 may be set by an authorized user 30 and/or be pre-configured at a default value. The device connection threshold value T1 may be any suitable value but may preferably be a value approximately equal to or greater than the configurable time interval I1, I2. If the data management system 20 determines in step 45 that the delta between the time of pump last connection time retrieval and the pump last connection time is greater than the device connection threshold T1, the data management system 20 may be configured to instruct the user interface 70 in step 45a to display a warning indicator for the pump on the user interface 70, upon which the interface 70 may display in step 46 the warning indicator next to the pump information. The warning indicator may alert the user 30 that the pump has not checked in within the connection threshold period T1 and/or that the pump may have lost connection to the data management system 20. If the data management system 20 determines in step 45 that the delta between the time of pump last connection time retrieval and the pump last connection time is equal to or less than the device connection threshold T1, the data management system 20 may be configured to instruct the user interface 70 to display the pump information without any warning indicator. A data management system configured to perform the aforementioned steps may enable a user to easily find out via the user interface whether a pump has not checked in within the connection threshold period T1 and/or whether the pump has lost connection to the data management system.

In an embodiment in which the user interface 70 is a monitor or touch screen, FIG. 3 depicts content displayed on the screen that an authorized user may see after the data management system 20 has determined at step 45 of FIG. 2 that the delta between the time of pump last connection time retrieval and the pump last connection time is greater than the device connection threshold T1, FIG. 3 shows the interface 70 displaying information for a pump 10a located at a hospital 50. A warning indicator graphic 47 is displayed next to the pump last connection time 42 to notify the user 30 that the pump 10a has not checked in within the connection threshold period T1 and/or that the pump has lost connection to the data management system 20.

Figure 4:
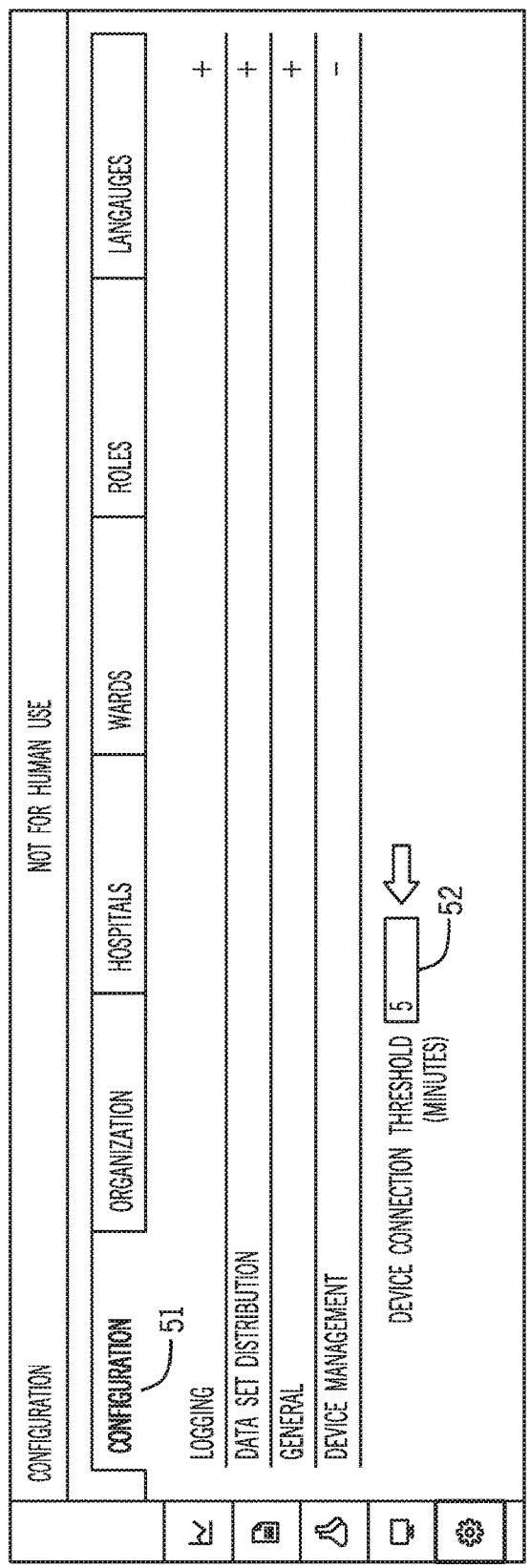
FIG. 4 is an illustration of content on a user interface where an authorized user can input value, according to an exemplary embodiment.

FIG. 4 depicts content displayed on the user interface 70 where an authorized user 30 may set the device connection threshold value T1 system parameter against which the difference delta between the time of pump last connection time retrieval and the pump last connection time may be compared in step 44a of FIG. 2. FIG. 4 shows the interface 70 displaying content within a configuration tab 51. An input field 52 for the device connection threshold value T1 system parameter may be located at the bottom of the screen. An authorized user 30 may input the device connection threshold value T1 into the input field 52. Although the input field 52 in FIG. 4 is shown to receive the threshold value T1 input in minutes, the input field 52 may be configured to receive input in any suitable unit of time, e.g., milliseconds, seconds, minutes, hours, days, etc.

Figure 5:
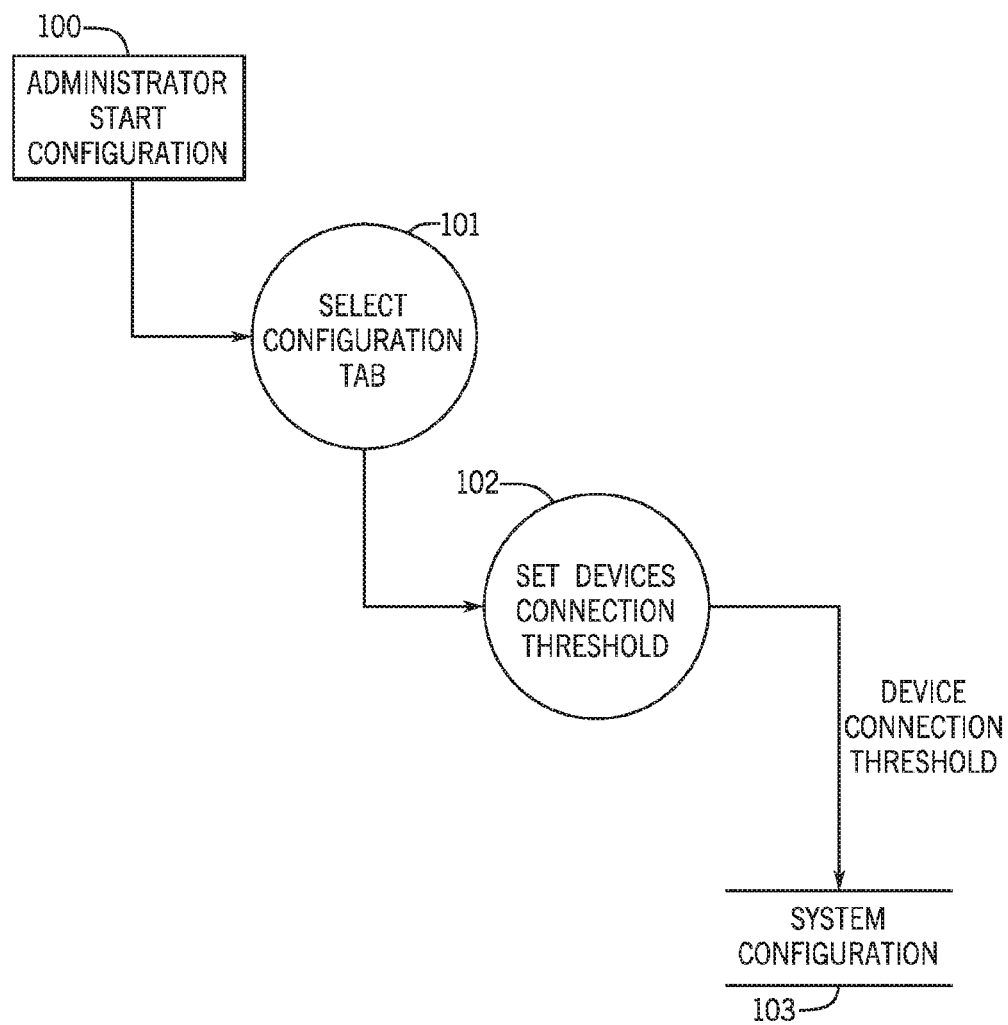
FIG. 5 is a flow diagram showing an overview of the steps for configuring a system parameter used to monitor connection status between a medical device and the data management system, according to an exemplary embodiment.

FIG. 5 is a flow diagram showing an overview of the steps for configuring a system parameter used to monitor connection status between a medical device and the data management system, according to an exemplary embodiment. After an authorized user begins the configuration process in step 100 by e.g., accessing the user interface, the authorized user may navigate at step 101 to a module in which settings may be configured, e.g., the configuration tab 51 of FIG. 4. Within the module, at step 102, the authorized user may input a system parameter, e.g., device connection threshold value T1, into an input field, and configure the system parameter into the data management system resulting in system configuration at step 103.

Figure 6:
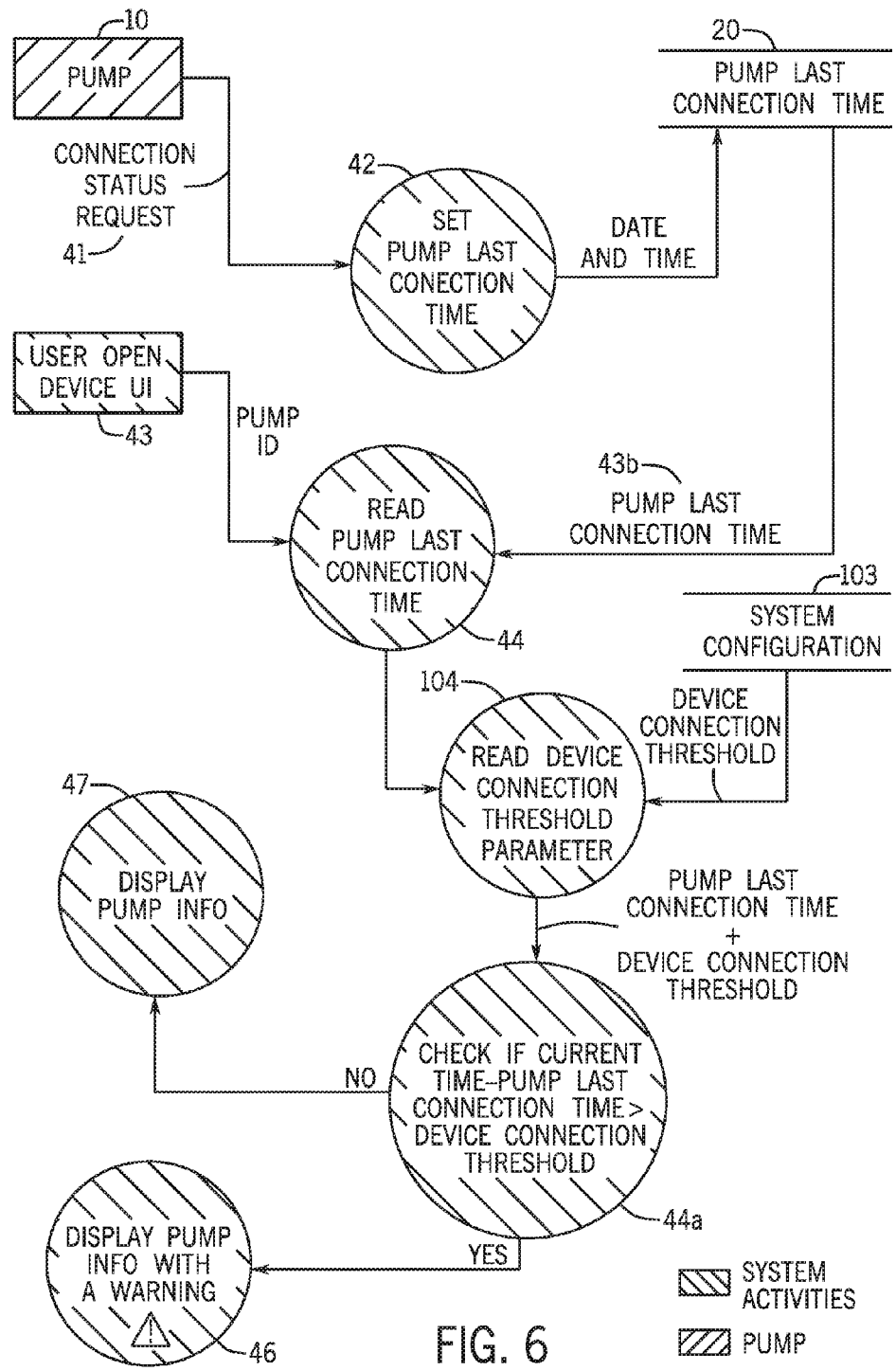
FIG. 6 is a flow diagram illustrating an overview of the process steps for monitoring connection status and notifying a user that a medical device has or has not checked in with a data management server computer within a threshold time period, according to an exemplary embodiment.

FIG. 6 is a flow diagram illustrating an overview of the process steps for monitoring connection status and notifying a user that a medical device has or has not checked in with a data management server computer within a threshold time period, according to an exemplary embodiment. At step 41 of FIG. 6, a pump 10 may send a connection status message to a data management system 20. Pump 10 may be configured to send a connection status message to the data management system 20 at a configurable time interval I1, I2 and/or the data management system 20 may be configured to request and receive a connection status update from the pump 10 at regular time interval I1, I2. At step 42, the data management system 20 may set a pump last connection time, defined as the date and time that the connection status message was successfully received over the network by the data management system 20 from the pump 10. The pump last connection time may be recorded for future use by the data management system 20. At step 43 a user may access the user interface, upon which the data management system 20 may be configured to retrieve pump last connection time in step 44. The data management system 20 may retrieve the pump last connection time at step 43b. In step 104, the data management system 20 may access the device connection threshold T1 system parameter. The device connection threshold T1 may have been previously configured by an authorized user in step 103 (FIG. 5) and/or may have been pre-configured at a default value. The data management system 20 may compare at step 44a the current time at the time of pump last connection time retrieval (step 44) to the pump last connection time retrieved at step 43b. The difference delta between the current time of pump last connection time retrieval and the pump last connection time may then be compared to the device connection threshold value T1 retrieved at step 104. If the delta value is greater than the threshold value T1, the data management system 20 may be configured to instruct the user interface to display a warning indicator for the pump on the user interface, upon which the interface may display in step 46 the warning indicator next to the pump information. If the data management system 20 determines in step 46 that the delta between the time of pump last connection time retrieval and the pump last connection time is equal to or less than the device connection threshold T1, the data management system 20 may be configured to instruct the user interface to display at step 47 the pump information without any warning indicator.

Figure 7:
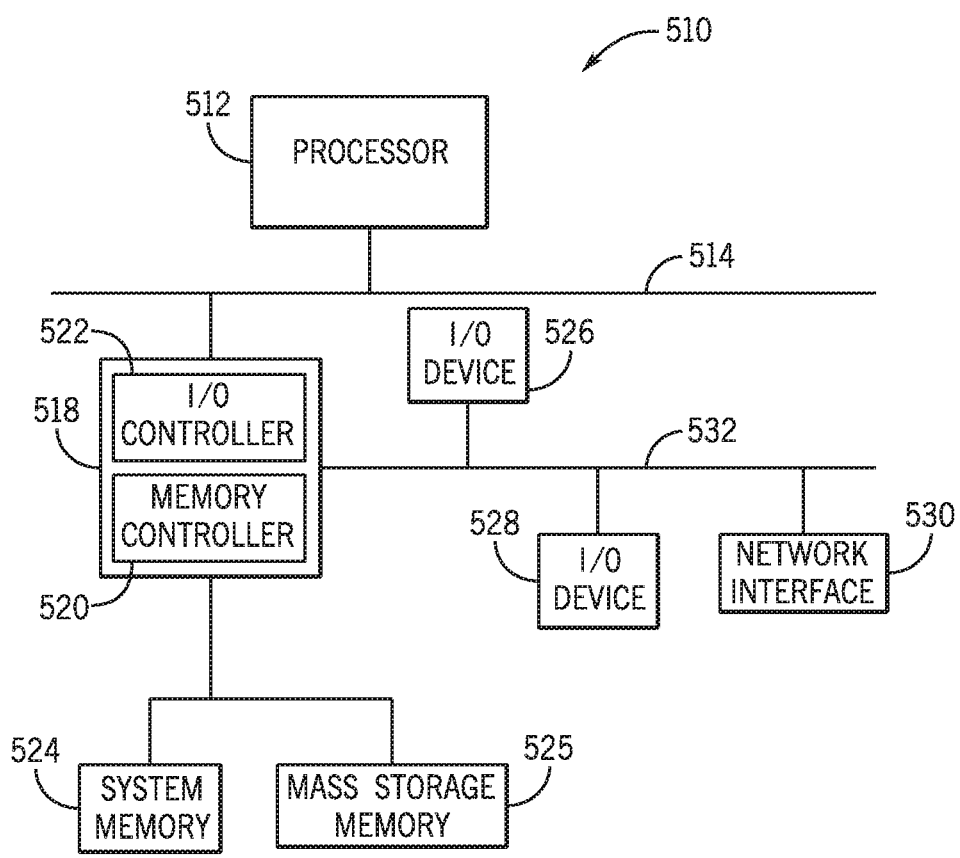
FIG. 7 is a block diagram of a data management system and/or server computer for processing medical device data for presentation on a display, according to an exemplary embodiment.

FIG. 7 is a block diagram of a data management system and/or server computer for processing medical device data for presentation on a display, according to an illustrative embodiment. In alternate embodiments, the systems and methods described herein may be implemented on a single server computer, a plurality of server computers, a server farm, a cloud server environment, or using other computer resources. Data management system/server 20 and medical devices 10, 10a may comprise analog and/or digital circuit components forming processing circuits configured to perform the steps described herein. The processing circuits may comprise discrete circuit elements and/or programmed integrated circuits, such as one or more microprocessors, micro-controllers, analog-to-digital converters, application-specific integrated circuits (ASICs), programmable logic, printed circuit boards, and/or other circuit components. Data management system/server 20 and medical devices 10, 10a may each comprise a network interface circuit configured to provide communications over one or more networks with each other and/or with other device. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of data management system/server 20. The database may be a DBMS hosted on a server host platform, such as Microsoft Windows XP, Microsoft Windows Server 2008, etc.

Referring again to FIG. 7, a block diagram of an example processor system 510 is shown that can be used to implement systems, articles of manufacture, and methods described herein. As shown in FIG. 7, the processor system 510 includes a processor 512 that is coupled to an interconnection bus 514. The processor 512 can be any suitable processor, processing unit, or microprocessor, for example. Although not shown in FIG. 7, the system 510 can be a multiprocessor system and, thus, can include one or more additional processors that are identical or similar to the processor 512 and that are communicatively coupled to the interconnection bus 514.

The processor 512 of FIG. 7 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc, that enables the processor system 510 to communicate with another processor system.

While the memory controller 520 and the I/O controller 522 are depicted in FIG. 7 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 7). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A medical device management system comprising:
   a medical device comprising a network interface circuit configured to provide communications over a network;
   a server computer configured to monitor and process medical device data for presentation on a user interface, comprising:
   a network interface circuit configured to provide communications over the network with the medical device; and
   a processing circuit configured to:
   receive at configurable time intervals a medical device connection status message from the medical device over the network, wherein the medical device is configured to send the connection status message to the server computer at said configurable time intervals;
   set a device last connection time, comprising a date and time that a most recent connection status message was received over the network by the server computer from the medical device;
   receive input from a user interface in communication with the server computer to retrieve medical device information;
   calculate a delta between the device last connection time and a date and time the processing circuit received the input from the user interface;
   compare the delta with a device connection threshold value, wherein the device connection threshold value is set equal to or greater than the configurable time interval; and
   display a warning indicator on the user interface if the delta is greater than the device connection threshold value.

2. The medical device management system of claim 1, wherein the device last connection time and the date and time the processing circuit received the input from the user interface are set in Coordinated Universal Time.

3. The medical device management system of claim 1, wherein the device connection threshold value and/or the configurable time interval are set by a user via the user interface.

4. The medical device management system of claim 3, wherein the user interface is configured to display a module having an input field configured to receive a value input from the user.

5. The medical device management system of claim 1, wherein the configurable time interval and/or device connection threshold value varies based on location, care area, ward, hospital, organization, geographical location, and/or different medical device modes, including in current active use mode, awake but inactive mode, sleep mode, and/or standby mode.

6. The medical device management system of claim 1, wherein the medical device comprises at least one of a blood collection device, apheresis device, biological fluid processing device, therapeutic device, infusion pump, medical laboratory device, and drug delivery pump.

7. The medical device management system of claim 6, wherein the medical device comprises an infusion pump comprising at least one of a large volume infusion pump, a patient-controlled analgesia pump, an elastomeric pump, a syringe pump, an enteral feeding pump, a parenteral feeding pump, and an insulin pump.

8. The medical device management system of claim 1, wherein the warning indicator is displayed on the user interface proximate to the device last connection time.

9. The medical device management system of claim 1, wherein the processing circuit is configured to not display a warning indicator on the user interface if the delta is equal to or less than the device connection threshold value.

10. A computer-implemented medical device management method for monitoring connection status between medical devices and their data management server computer over a network, said method comprising:
   receiving at configurable time intervals via a processing circuit a medical device connection status message from a medical device over the network, wherein the medical device is configured to send the connection status message to the data management server computer at said configurable time intervals;
   setting a device last connection time, comprising a date and time that a most recent connection status message was received over the network by the server computer from the medical device;
   receiving input from a user interface in communication with the server computer to retrieve medical device information;
   calculating a delta between the device last connection time and a date and time the server computer received the input from the user interface;

comparing the delta with a device connection threshold value, wherein the device connection threshold value is set equal to or greater than the configurable time interval; and displaying a warning indicator on the user interface if the delta is greater than the device connection threshold value.

11. The method of claim 10, wherein the device last connection time and the date and time the server computer received the input from the user interface are set in Coordinated Universal Time.

12. The method of claim 10, wherein the device connection threshold value and/or the configurable time interval are set by a user via the user interface.

13. The method of claim 12, wherein the user interface is configured to display a module having an input field configured to receive a value input from the user.

14. The method of claim 13, wherein the configurable time interval and/or device connection threshold value varies based on location, care area, ward, hospital, organization, geographical location, and/or different medical device modes, including in current active use mode, awake but inactive mode, sleep mode, and/or standby mode.

15. The method of claim 10, wherein the medical device comprises at least one of a blood collection device, apheresis device, biological fluid processing device, therapeutic device, infusion pump, medical laboratory device, and drug delivery pump.

16. The method of claim 15, wherein the medical device comprises an infusion pump comprising at least one of a large volume infusion pump, a patient-controlled analgesia pump, an elastomeric pump, a syringe pump, an enteral feeding pump, a parenteral feeding pump, and an insulin pump.

17. The method of claim 10, wherein the warning indicator is displayed on the user interface proximate to the device last connection time.

18. The method of claim 10, wherein the processing circuit is configured to not display a warning indicator on the user interface if the delta is equal to or less than the device connection threshold value.

* * * * *